US007229474B2

United States Patent
Hoffmann et al.

(10) Patent No.: US 7,229,474 B2
(45) Date of Patent: Jun. 12, 2007

(54) METHOD FOR CONTROLLING THE POSITION OF A PERMANENT MAGNETICALLY SUPPORTED ROTATING COMPONENT

(75) Inventors: Jan Hoffmann, Berlin (DE); Andreas Arndt, Berlin (DE); Tobias Merkel, Kleinmachnow (DE)

(73) Assignee: Berlin Heart AG, Berlin (DE)

( * ) Notice: Subject to any disclaimer, the term of this patent is extended or adjusted under 35 U.S.C. 154(b) by 656 days.

(21) Appl. No.: 10/297,143

(22) PCT Filed: Apr. 29, 2002

(86) PCT No.: PCT/EP02/04737

§ 371 (c)(1),
(2), (4) Date: May 21, 2003

(87) PCT Pub. No.: WO02/088548

PCT Pub. Date: Nov. 7, 2002

(65) Prior Publication Data

US 2003/0187321 A1 Oct. 2, 2003

(30) Foreign Application Priority Data

Apr. 30, 2001 (DE) ................ 101 23 138

(51) Int. Cl.
*A61M 1/12* (2006.01)
(52) U.S. Cl. .............. 623/3.13; 623/3.28; 600/17
(58) Field of Classification Search .............. 606/16; 600/16, 17; 623/3.13–3.15, 3.1, 3.24, 3.25, 623/3.27, 3.28
See application file for complete search history.

(56) References Cited

U.S. PATENT DOCUMENTS

| 4,763,032 A | 8/1988 | Bramm et al. |
| 4,779,614 A | 10/1988 | Moise |
| 4,944,748 A | 7/1990 | Bramm et al. |
| 5,078,741 A | 1/1992 | Bramm et al. |
| 5,112,200 A | 5/1992 | Isaacson et al. |
| 5,126,610 A | 6/1992 | Fremerey |
| 5,211,546 A | 5/1993 | Isaacson et al. |
| 5,326,344 A | 7/1994 | Bramm et al. |
| 5,385,581 A | 1/1995 | Bramm et al. |

(Continued)

FOREIGN PATENT DOCUMENTS

JP 06-147808 5/1994

(Continued)

*Primary Examiner*—George R. Evanisko
(74) *Attorney, Agent, or Firm*—Brinks Hofer Gilson & Lione

(57) ABSTRACT

Since disruptive forces can be continuously exerted upon a rotor during a pulsatile flow through a pump with a magnetically mounted rotor (permanent magnets and addition control current coils), it is necessary to adjust position i.e. modify axial rotor position very quickly. The control current should only result in small amounts of losses. According to the invention, the current is pulse-width modulated by the control current coils by means of a set value predetermined by a controller which is arranged downstream from a position sensing system. If the set value is high, it is switched to a higher voltage level and the real value of the position sensing system is stored for a defined period of time, respectively beginning with the switching flank of the control current, and the position sensing system is disconnected during said period of time.

6 Claims, 3 Drawing Sheets

U.S. PATENT DOCUMENTS

| | | |
|---|---|---|
| 5,399,074 A | 3/1995 | Nose et al. |
| 5,405,251 A | 4/1995 | Sipin |
| 5,507,629 A | 4/1996 | Jarvik |
| 5,575,630 A | 11/1996 | Nakazawa et al. |
| 5,588,812 A | 12/1996 | Taylor et al. |
| 5,601,418 A | 2/1997 | Ohara et al. |
| 5,676,162 A * | 10/1997 | Larson et al. ............... 128/899 |
| 5,683,231 A | 11/1997 | Nakazawa et al. |
| 5,686,772 A | 11/1997 | Delamare et al. |
| 5,695,471 A | 12/1997 | Wampler |
| 5,707,218 A | 1/1998 | Maher et al. |
| 5,725,357 A * | 3/1998 | Nakazeki et al. ............. 417/18 |
| 5,729,065 A | 3/1998 | Fremery et al. |
| 5,746,575 A | 5/1998 | Westphal et al. |
| 5,803,720 A | 9/1998 | Ohara et al. |
| 5,863,179 A | 1/1999 | Westphal et al. |
| 5,911,558 A * | 6/1999 | Nakazeki et al. ........... 415/118 |
| 5,947,703 A | 9/1999 | Nojiri et al. |
| 6,015,272 A | 1/2000 | Antaki et al. |
| 6,071,093 A * | 6/2000 | Hart ........................ 417/424.2 |
| 6,080,133 A | 6/2000 | Wampler |
| 6,100,618 A | 8/2000 | Schoeb et al. |
| 6,234,998 B1 | 5/2001 | Wampler |
| 6,368,083 B1 | 4/2002 | Wampler |
| 6,688,861 B2 | 2/2004 | Wampler |
| 2001/0053330 A1* | 12/2001 | Ozaki ........................ 417/420 |
| 2002/0094281 A1 | 7/2002 | Khanwilkar et al. |
| 2002/0102169 A1 | 8/2002 | Wampler |
| 2004/0234397 A1 | 11/2004 | Wampler |

FOREIGN PATENT DOCUMENTS

| | | |
|---|---|---|
| JP | 08-028563 | 2/1996 |
| JP | 10-201273 | 7/1998 |
| WO | WO 00 64030 | 10/2000 |
| WO | WO 00/64030 | 11/2000 |
| WO | WO 00 74748 | 12/2000 |

* cited by examiner

METHOD FOR CONTROLLING THE POSITION OF A PERMANENT MAGNETICALLY SUPPORTED ROTATING COMPONENT

BACKGROUND OF THE INVENTION

The invention relates to a method for controlling the position of a permanent magnetically supported rotating component, e.g. of the rotor of a synchronous motor without brushes, by means of a position determination of this component by means of a position sensory analysis and additional control current coils, influencing the magnetic field of the permanent magnetic support and which current value is determined by the position of the component. The synchronous motor can for example serve as a drive for an axial fluid delivery pump.

Multiphase fluids, e.g. emulsions and dispersions with a low stability can easily reach into instable areas during the delivery in corresponding delivery systems.

An especially sensitive fluid is blood. Blood is hermetically shielded in the natural recirculation system from the environment, so that no foreign interferences are acting upon it. If, however, the necessity exists, to substitute the heart by an artificial blood pump or to support the recirculation by an additional heart pump, reactions of the blood with the technical system are produced. The blood is subjected, then, easily to the haemolysis or the formation of thrombus with the corresponding disadvantageous effects for the patient. Therefore, recently large efforts were made, to form fluid delivery pumps in such a way, that the blood or other sensitive fluids are subjected to the lowest possible mechanical influences. One possibility for this is the magnetic support of the rotating element of a pump drive. The advantage of the magnetic support is not only, that no components mechanically in a frictional way are present any more, but that also the achievable rotational acceleration of the rotating element is increased and the controllability of the rotational speed and therewith, of the volume flow can be improved.

Such a fluid pump can be integrated in the known way in a synchronous motor without brushes. The fluid pump consists according to WO 00/640 30 essentially of a cylindrical tube, which can be connected at both sides to a fluid system. The tube is surrounded by the stator, consisting of the metal packet, the winding and the iron flux return hood. The rotor comprises permanent magnetic field exciters and has on its outer cover delivery devices for the fluid, so that the fluid can be axially delivered in the annular space between the tube and the rotor.

The rotor is magnetically supported. It carries for the purpose on its both end sides cylindrical or annular permanent magnets attached thereon, which are magnetised in the axial direction. The permanent magnets of the rotor are opposed by counter magnetised permanent magnets, which e.g. can be arranged in the end sides of guiding devices, which themselves are mounted in the cylindrical tube.

Both magnet pairs act stabilisingly in radial direction, when they are orientated to attract each other, i.e., the radial support is passively stable. The rotor is, however, instable in the axial direction.

Without additional stabilisation the rotor would be attracted by one of the two pairs of permanent magnets. Therefore, control coils are arranged on the stator sides in such a way, that a current weakens by the in series connected control coils the magnetic field of one of the pairs of permanent magnets and increases the magnetic field of the other pair of permanent magnets. The control current has to be adjusted in dependency of the actual axial rotor position. For this, the rotor position has to be determined by means of position sensors.

The position sensors consist for example of two sensor coils, which can be arranged on the end sides of the guiding devices. The sensor coils are opposed on the ends of the rotor by aluminium bodies, in which eddy currents are formed, when the sensor coils are loaded by an alternating current. By the axial movement of the rotor a change in the inductance of the sensor coils is produced, which in an arrangement in a bridge connection can be evaluated as a measuring signal for the rotor position.

As especially in a pulsating flow through the pump disturbing forces act continuously on the rotor, the position control has to be able to quickly adjust a changed axial rotor position. On the other hand the control current should cause a low dissipation, which is especially important for blood pumps, as the produced heat energy should be kept as small as possible. Furthermore, the drive energy has to be taken from implanted batteries, which operation time should be as long as possible.

SUMMARY OF THE INVENTION

An aspect of the invention is to provide a method for controlling the position of a magnetically supported component, with which a dissipation of the control of the position can be kept small.

The aspect of the invention is described by the features of claim 1. Suitable embodiments are subject of the dependent claims.

According to this the current through the control current coils is pulse width modulated according to a desired value, to which a controller arranged behind the position sensory analysis is set, wherein at a high desired value a switching to a higher voltage level takes place. This has the advantage, that the adjustment times can be kept very small and the necessary power can still be kept low.

The actual value of the position sensory analysis is stored for a defined time interval, respectively starting latest with the pulse edge of the control current and the position sensory analysis is stopped during this time interval.

Advantageously in the use of the position control in a synchronous motor without brushes, the actual value of the position sensory analysis is also temporarily stored in reference to the gatting impulse of the motor coils for a defined time interval, starting latest with the pulse edge of the gatting impulse, and the position sensory analysis is stopped for this time interval.

The interferences produced by the timing concerning the position determination are controlled by the stopping of the measuring during these time periods and by the storing of the measured values.

For specific applications it can be suitable, to take the square of the desired value of the controller arranged behind the position sensory analysis mechanism and to stop the position adjustment at a time-averaged overshooting of the threshold of this value until the next undershooting of the threshold. Thus, a rise in temperature of the control coils is reproduced and therefore, an overheating is prevented.

Appropriately, a PID-controller with an $I_2$-component is used for the controller arranged behind the position sensory analysis mechanism.

BRIEF DESCRIPTION OF THE DRAWINGS

The invention is described in detail by means of an embodiment. In the corresponding drawings.

DETAILED DESCRIPTION OF THE PREFERRED EMBODIMENTS

Figure 1:
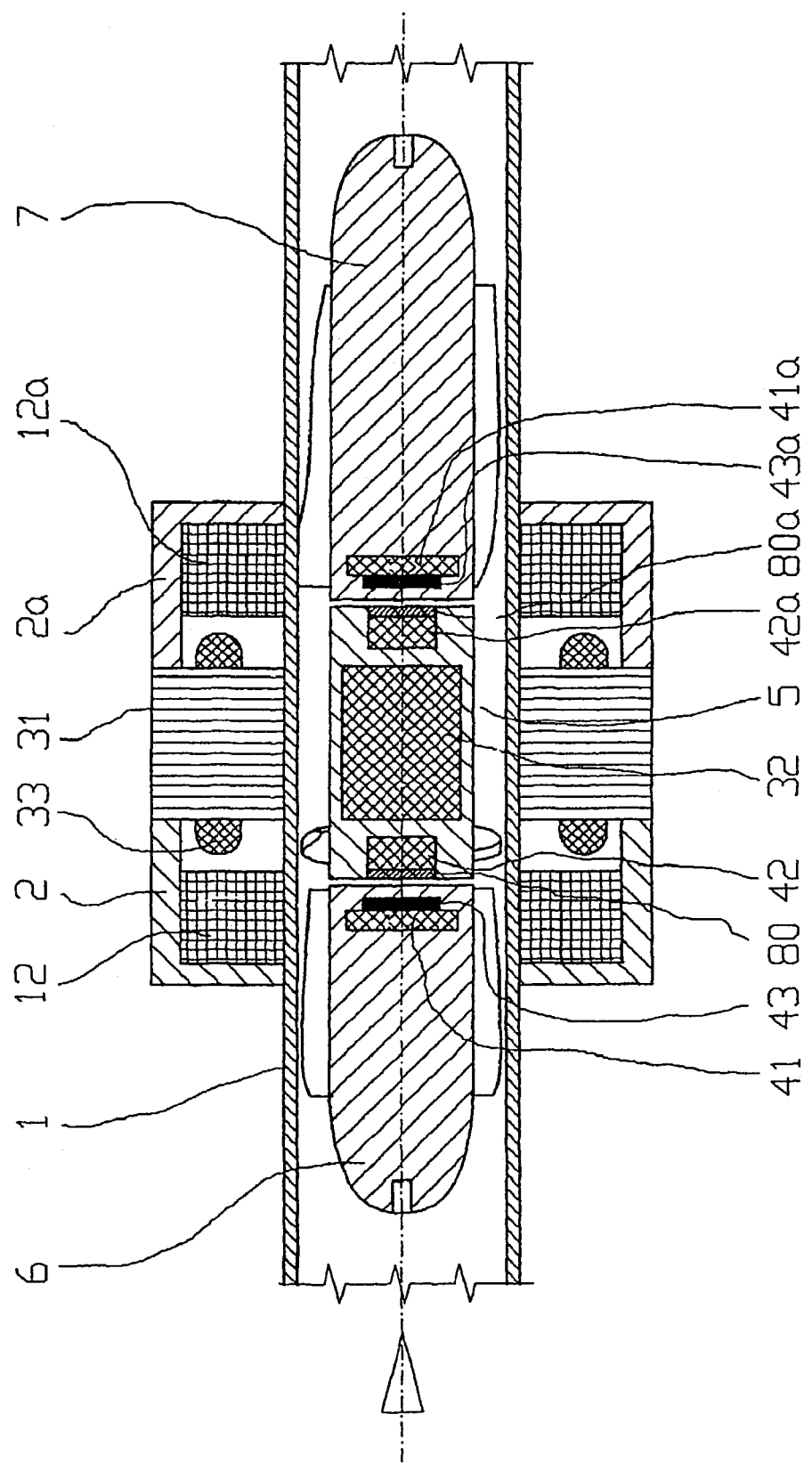
FIG. 1 shows a sectional view through a fluid delivery pump, which is suitable for the execution of the method according to the invention.

FIG. 1 shows such an axial pump suitable for the execution of the method. The drive of the blood pump works according to the principal of an electronic commutated synchronous motor. The motor has a stator, consisting of a metal sheet packet 31, of windings 33 and iron flux return hoods 2, 2a and a rotor 5 with a permanent magnetic core 32. The stator encloses a tubular hollow body 1, in which in axial direction a fluid, in the present case blood, is delivered. The rotor 5 is supported magnetically free of contact.

The magnetical support (bearing) consists of permanent magnets 42, 42a on the rotor end sides and permanent magnets 41, 41a on the end sides of the guiding devices 6 and 7. The guiding devices 6, 7 are mounted on the inner wall of the tubular hollow body 1.

To the magnetic support (bearing) further belong control coils 12, 12a. Sensor coils 43, 43a in the guiding devices 6, 7 and short circuit rings 80, 80a arranged opposed thereto, serve for measuring the actual rotor position.

The pairs of permanent magnets 41, 42; 41a, 42a are, respectively, polarised for attracting each other. Magnetically the pairs are arranged in series.

Without an additional stabilisation the rotor 5 would, however, be attracted to one side, therefore. An instable equilibrium exists in axial direction. In radial direction both magnet pairs act self-centering, and, therefore, the radial position is passively stable.

The control coils 12, 12a are connected electrically in series and are magnetically arranged in such a way, that a current weakens the magnetic field of the one pair of magnets and increases the magnetic field of the other pair. The magnetic flux return path is produced via the iron flux return hoods 2, 2a and the metal sheet packet 31 of the stator.

The axial position of the rotor 5 can be determined by means of the sensor coils 43, 43a. The sensor coils 43, 43a are loaded by a higher frequent voltage. By the axial movement of the rotor 5 a change of the inductivity of the sensor coils 43, 43a is produced. By the arrangement of the sensor coils 43, 43a in a bridge connection a measuring signal for the axial position of the rotor 5 can be achieved.

Figure 2:
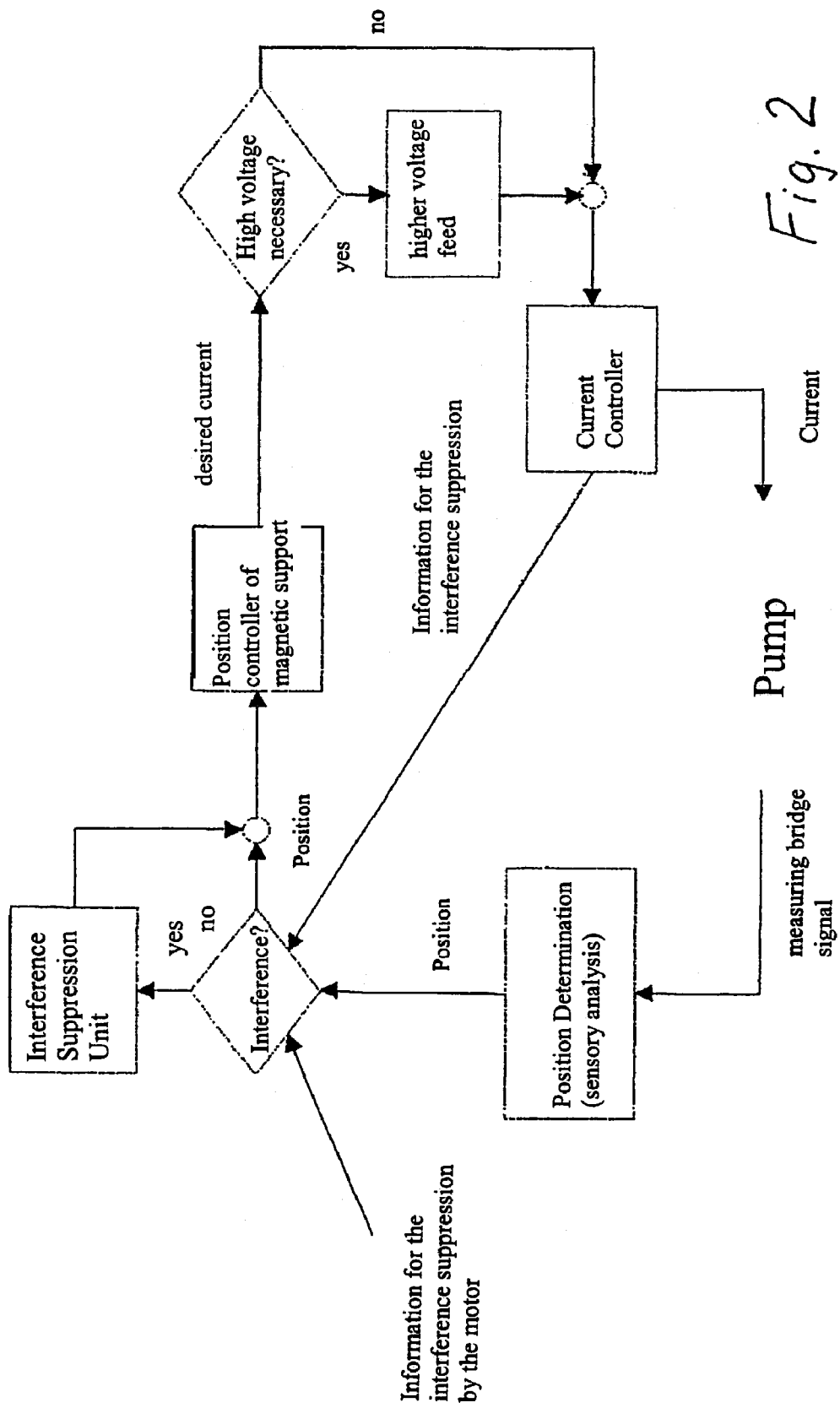
FIG. 2 shows a representation of the principal of the position control with the additional flow control according to the invention.

As shown in FIG. 2, at the outlet of a controller, arranged behind the position sensory analysis mechanism, an operating value of the control current is produced by the control coils 12, 12a. The control current is transmitted by means of a current controller to the control coils 12, 12a. The current controller acts as a closed control circle, i.e. it measures the current by means of the control coils 12, 12a and compares the result with a default value (desired current) of the position controller. By means of a pulse width modulation of a pulsed power stage the actual current is adjusted to the desired current. This process necessitates a specific time, which depends on the difference of the desired current and the actual current. The higher the voltage is, with which the power stage operates, the shorter is the adjustment time of the current controller. On the other hand the dissipation in the power stage increases with the voltage. To be able to achieve a quick reaction of the current controller and a lower dissipation, a higher voltage is additionally switched on, only when a large difference between the desired current and the actual current is present; otherwise it operates with a lower voltage.

By the excitation of the control coils 12, 12a by means of the pulsed power stage interferences, which can disturb the position determination of the rotor 5, are produced in the sensor coils 43, 43a. These interferences couple with each pulse edge on the control coils 12, 12a to the sensor coils 43, 43a and fade out after a defined time interval. Therefore, for the expected time interval of these interferences, the position signal, achieved directly beforehand, is temporarily stored and the position determination is stopped. The position controller works during this time interval with the stored value. When the interference is faded out, the position is again determined by means of the sensor coils 43, 43a. Similar interferences can also be produced by the excitation of the windings 33. Also for these the method of the temporary storing is used. The electronics of the interference suppression receive from the current controller and from the excitation electronics of the motor the exact time of the possible starting point of the interferences, so that they can store the position signals.

Figure 3:
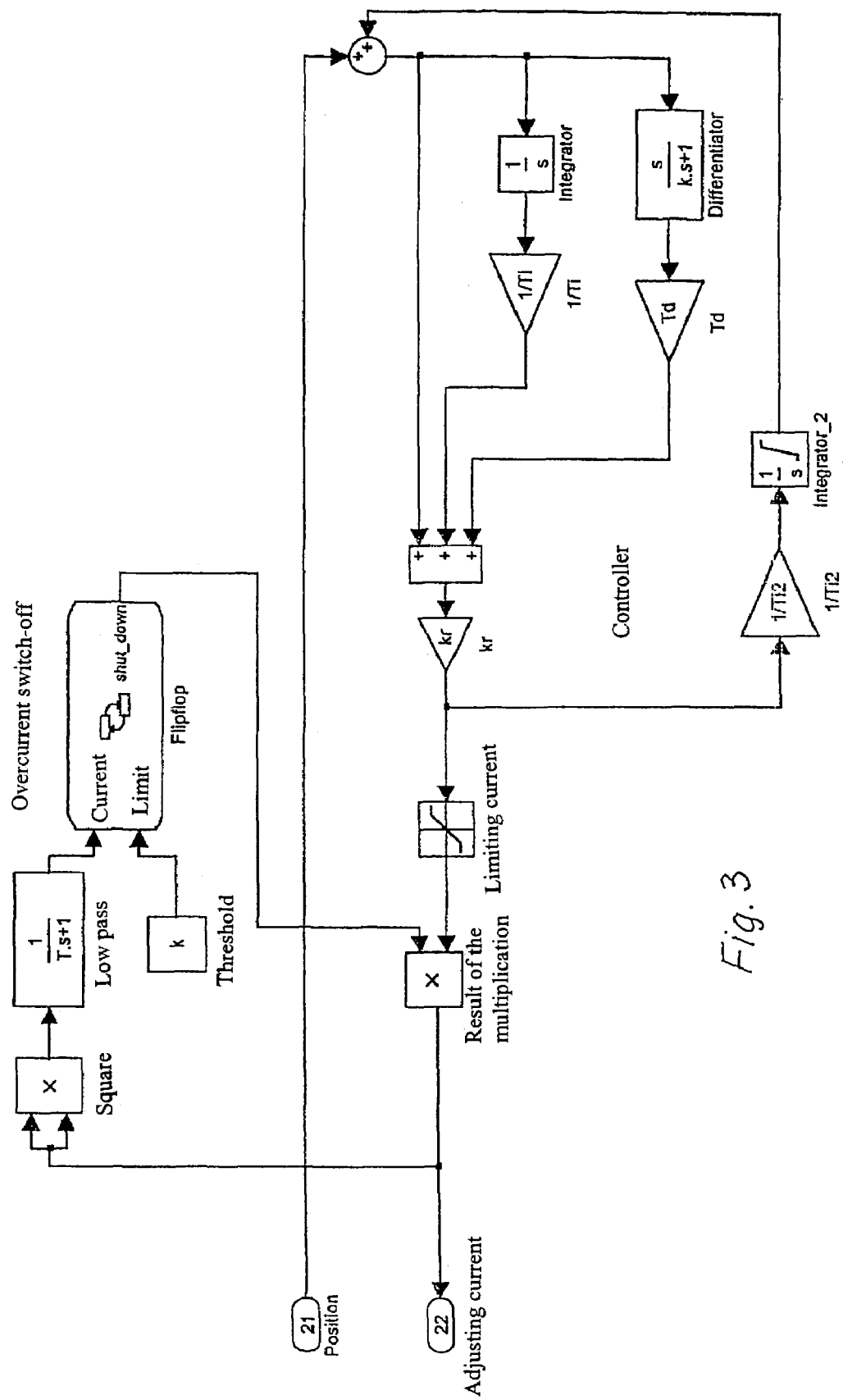
FIG. 3 shows a block circuit diagram of the position controller.

FIG. 3 shows the circuitry for the position control of the magnetic support. From the measured position of the rotor, which loads the path 21, a set current for the control coils 12, 12a, which leads to a secure hovering of the rotor 5 in all operating conditions, is determined and transmitted to the outlet 22 of the position controller. The position controller consists of a PID-controller, which is characterised by the time constants of the integrator Ti and of the differentiator Td as well as by the multiplication factor kr of a variable gain amplifier. To protect the control coils 12, 12a against a thermal overload the to be expected dissipation is additionally determined from the current square. During a threshold overshooting time averaged over a low-pass, the position control is switched-off, until the threshold is again undershot. The position controller has as an additional function, to keep the current through the control coils 12, 12a as low as possible. By means of an integrator ($I_2$-component) the set current is coupled back to the controller inlet. As a result the rotor 5 is always positioned at the axial position in the pump, at which only a minimal current flows through the control coils 12, 12a.

Reference numerals list
1 Tubular hollow body
2 Iron flux return hood
2a Iron flux return hood
5 Rotor
6 Guiding device
7 Guiding device
12 Control coil
12a Control coil
31 Metal sheet packet
32 Permanent magnetic core
33 Windings
41 Permanent magnet
41a Permanent magnet
42 Permanent magnet
42a Permanent magnet
43 Sensor coil 43a Sensor coil
21 Path
22 Outlet
80 Short circuit ring
80a Short circuit ring
Ti Integrator
Td Differentiator
kr Multiplication factor

What is claimed is:

1. A method for controlling the position of a permanent magnetically supported rotating component, providing the steps of
   determining the position of the component through a position sensory analysis mechanism;
   providing control current coils for influencing the magnetic field of the permanent magnetic support;
   providing an adjustable current through the control current coils, the adjustable current being determined by the position of the component, wherein the current, through the control current coil, is pulse width modulated according to a predefined value, set in a controller coupled to the position sensory analysis mechanism,
   switching the adjustable current to a higher voltage stage when a higher desired value is required by the controller, and
   storing the actual value of the position sensory analysis for a defined time interval, starting respectively at the latest with the pulse edge of the control current, and stopping the position sensory analysis for the defined time interval.

2. The method according to claim 1, wherein the rotating component is driven by a synchronous brushless motor having motor windings excitable by a pulse width modulated excitation current having pulse edges, the method further comprising the step of temporarily storing the actual value of the position sensory analysis for a second defined time interval, starting at the latest with the pulse edge of the excitation impulses and stopping the position sensory analysis for this seecond time interval.

3. The method according to claim 1, further comprising a step of:
   providing a PID-controller with an $I_2$-component for the controller coupled to the position sensory analysis mechanism.

4. A method for controlling the position of a permanent magnetically supported rotating component, providing the steps of
   providing a position sensor arrangement;
   providing control current coils capable of influencing the magnetic field of the permanent magnetic support;
   determining the current amount by the position of the rotating component, by adjusting the pulse width of the current through the control current coils, the pulse width being modulated according to a predefined value, set in a controller connected to the position sensory arrangement, and wherein at a high predefined value, switching the current to a higher voltage and storing the actual value of the position sensor arrangement for a defined time interval starting respectively at the latest with the pulse edge of the control current, and stopping the position sensory analysis for said defined time interval.

5. A method for adjusting the position of a rotating component, which is supported by means of a permanent magnet and coils carrying a controlled current influencing the magnetic field of the permanent magnet, the method comprising the steps of:
   sensing the position of the rotating component with a position sensor,
   controlling the current delivered to the coils by varying the width of the current pulses based on the sensed position of the rotating component to achieve a target value;
   switching the current to a higher voltage if the target value is too high to be achieved by pulse width modulation;
   storing the sensed position of the rotating component for a defined period beginning, at the latest, with the pulse edge of the control current; and
   deactivating the position sensor during said defined period.

6. The method of claim 1 or 5 further comprising the steps of:
   calculating the square of the target value specified by the controller connected to the output of the position sensor;
   deactivating the position sensor whenever the time averaged value of the square of the target value exceeds a threshold value; and
   maintaining the deactivation of the position sensor until the square of the target value drops below the threshold value.

* * * * *

UNITED STATES PATENT AND TRADEMARK OFFICE
CERTIFICATE OF CORRECTION

PATENT NO.         : 7,229,474 B2
APPLICATION NO.    : 10/297143
DATED              : June 12, 2007
INVENTOR(S)        : Jan Hoffmann et al.

It is certified that error appears in the above-identified patent and that said Letters Patent is hereby corrected as shown below:

Column 5
Line 20, delete "coil" and insert --coils--.

Signed and Sealed this

Thirty-first Day of July, 2007

JON W. DUDAS
*Director of the United States Patent and Trademark Office*